United States Patent [19]

Benton et al.

[11] 4,246,302
[45] Jan. 20, 1981

[54] MULTI-BAND LIQUID CRYSTAL FILM LAMINATE

[76] Inventors: William J. Benton, 1046 Murray Hill Ave., Pittsburgh, Pa. 15217; Joseph R. Quigley, 7425 Ben Hur St., Pittsburgh, Pa. 15208

[21] Appl. No.: 52,819

[22] Filed: Jun. 27, 1979

[51] Int. Cl.³ ............................................. B32B 31/20
[52] U.S. Cl. ................................. 428/1; 428/423.1; 428/423.7; 428/913
[58] Field of Search ............. 428/1, 913, 425, 423.1, 428/423.7

[56] References Cited

U.S. PATENT DOCUMENTS

| | | | |
|---|---|---|---|
| 3,872,050 | 3/1975 | Benton | 428/1 |
| 3,886,014 | 5/1975 | Bayer | 428/1 |

*Primary Examiner*—Marion McCamish
*Attorney, Agent, or Firm*—Harry B. Keck

[57] ABSTRACT

A multi-band liquid crystal film for visual observation of two or more patterns is prepared by laminating at least two polyurethane films, each containing discrete aggregates of liquid crystals against a black film such that the visual response of the liquid crystals of each succeeding polyurethane film is different than that of the liquid crystals in the other film or films.

13 Claims, 11 Drawing Figures

MULTI-BAND LIQUID CRYSTAL FILM LAMINATE

BACKGROUND OF THE INVENTION

1. Field of the Invention

Liquid crystal film laminates.

2. Description of the Prior Art

Liquid crystal films have employed liquid crystal compositions encapsulated in suitable encapsulating vehicles as single films. Only a single visual temperature has been available for any one film in the prior art.

A technique for preparing polyurethane films containing discrete aggregates of liquid crystal compositions has been described in U.S. Pat. No. 3,872,050. Such polyurethane films can be employed, in accordance with prior art teachings, to prepare a single visual response sensing film.

SUMMARY OF THE INVENTION

A multi-band liquid crystal thermographic film is prepared by laminating at least two polyurethane films, each film containing discrete aggregates of liquid crystal compositions of differing response characteristics. In one embodiment, the individual films contain liquid crystals having differing temperature response levels. The highest temperature response level film is laminated to a black film base.

In another embodiment, the individual films contain temperature stabilized liquid crystal compositions which exhibit differing color responses, for example, a green response in one film and a red response in another film. This embodiment is particularly useful for generating circularly polarized light.

In a still further embodiment, one film may be temperature responsive and the other film may be temperature stabilized to respond with a selected color.

A transparent barrier is applied to the first polyurethane film. A second polyurethane film containing discrete aggregates of liquid crystal composition is applied to the first transparent barrier. A second transparent barrier is applied to the exposed surface of the second polyurethane film. If desired, third, fourth, fifth and even more polyurethane films containing discrete aggregates of liquid crystal compositions may be applied with a transparent barrier interposed between each polyurethane film. When temperature-responsive liquid crystals are employed, the response temperature of the liquid crystal compositions of each succeeding polyurethane film should be lower than that of the liquid crystal compositions of the previously deposited film. The polyurethane films preferably range in thickness from 5 to 100 microns. Films of about 20 microns thickness are optimum. The films are prepared in accordance with the teachings of U.S. Pat. No. 3,872,050 and preferably in accordance with the teachings of copending application Ser. No. 915,556 filed June 14, 1978, a continuation-in-part of earlier filed application Ser. No. 706,962 filed July 20, 1976. Such films contain from 5 to 50 percent by weight of liquid crystal composition. The liquid crystals may include suitable dark dyes to improve the visibility of the color response of the liquid crystals. The liquid crystal aggregates preferably are dispersed in discrete aggregates having particle sizes from 0.1 to 20 microns, but of course, smaller than the thickness of the polyurethane film in which the aggregates are dispersed.

DESCRIPTION OF THE PREFERRED EMBODIMENT(s)

Figure 1:
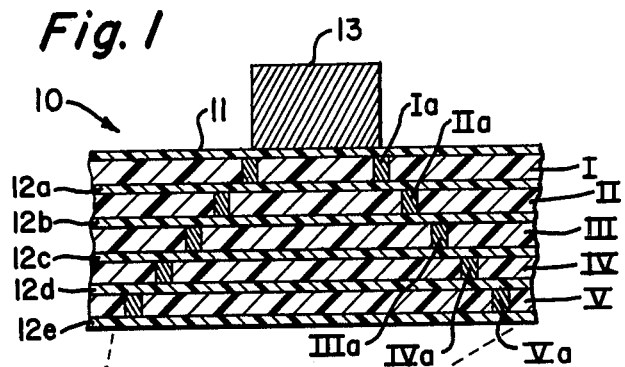
FIG. 1 illustrates in cross-section a laminate according to the present invention containing five polyurethane films.

As shown in FIG. 1, a laminate 10 is prepared by laminating sequentially a black base film 11, a series of polyurethane films I, II, III, IV, V. A transparent barrier 12a, 12b, 12c, 12d is provided between the films I-II, II-III, III-IV, IV-V, respectively. An outer transparent coating 12e is applied to the exposed surface of the polyurethane film V. The transparent barriers 12a, 12b, 12c, 12d and the outer coating 12e are preferably about 1 micron in thickness. Monomolecular coatings might be employed as the transparent barrier film. Suitable barrier materials include polyethylene terephthalate film, a transparent polyurethane film, an aqueous gelatin film, and in general any transparent material which is impervious to diffusion of materials that may contaminate the liquid crystal film.

Figure 2:
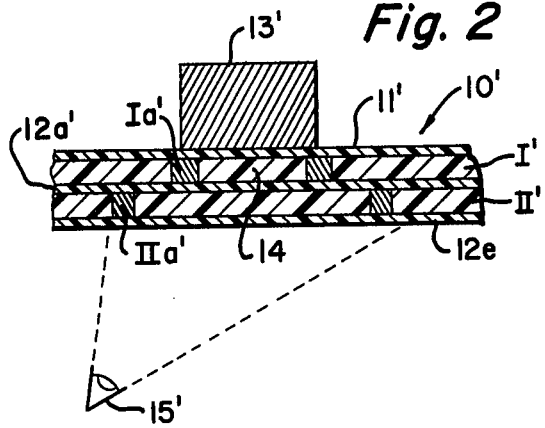
FIG. 2 contains a laminate according to the present invention containing two polyurethane films.

In FIG. 2 there is illustrated a laminate 10' having two layers of polyurethane film I', II' laminated to a black base film 11' and separated by a transparent barrier 12'a. An outer transparent coating 12'e is applied over the second polyurethane film II'.

In a typical laminate, of the type shown in FIG. 1, the liquid crystal compositions in polyurethane films have response temperatures set forth in the following table:

| Film | Response Temperature |
| --- | --- |
| V | 80–82° F. |
| IV | 82–84° F. |
| III | 84–86° F. |
| II | 86–88° F. |
| I | 88–90° F. |

Figure 4:
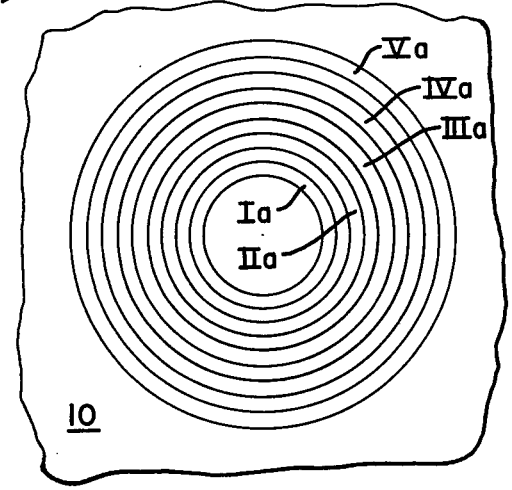
FIG. 4 is a representation of the visual response of the laminate of FIG. 1.

When a heat source 13 is applied to the laminate 10 of FIG. 1, the laminate 10 quickly reaches equilibrium with the heat source 13 and the color responses occur in annular rings Ia, IIa, IIIa, IVa, Va as shown in FIG. 1 and in FIG. 4. FIG. 4 shows the visual response as seen by an observer at 15, FIG. 1. The visual appearance of the laminate in FIG. 4 provides a thermal map of the surface underlying the black base film 11.

Figure 3:
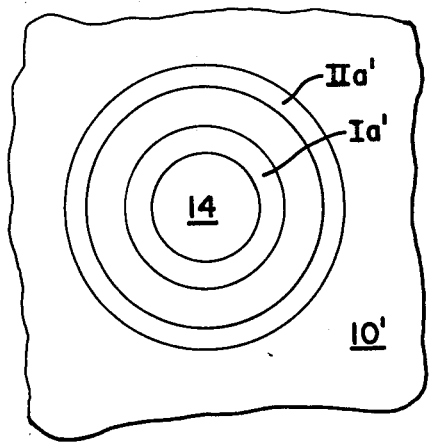
FIG. 3 is an illustration of the visual response of the film of FIG. 2.

Similarly, when a heat source 13' is applied to the laminate of FIG. 2, the visual representation to an observer at 15' is shown in FIG. 3 wherein a black core 14 appears to be surrounded by annular rings I'a, II'a.

PREFERRED EMBODIMENTS

It is possible to apply the polyurethane films by curing them directly as films in sequence to form the laminate of FIG. 1 or FIG. 2. A preferred procedure is to prepare the polyurethane films as separate products and to apply the preformed polyurethane films, each containing discrete aggregates of liquid crystal exhibiting the selected temperature response.

The temperature sensitivity according to the present invention can be achieved readily over a temperature range from sub-zero centigrade to about 100° centigrade.

For biomedical purposes, response temperatures of 85° to 105° F. are useful. Other ranges are useful in various non-destructive analytical applications.

As the temperature sensitive liquid crystals pass through the response temperature, they exhibit a color change from blue to green to yellow to red to black. When a blue color of one film overlaps a red color of another film, a magenta band may appear. Each of the individual layers will exhibit the color transition phenomenon in a repeatable and observable manner.

Figure 5:
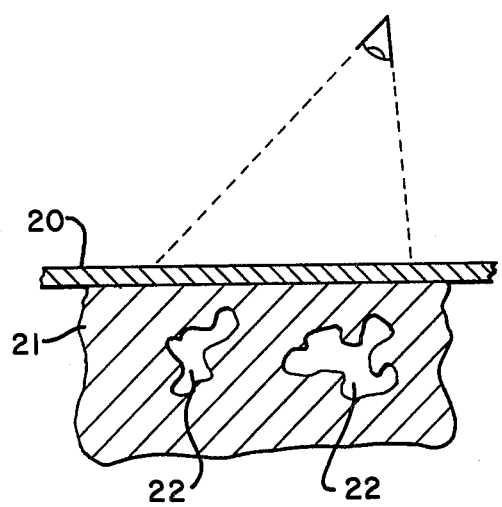
FIG. 5 is a fragmentary cross-sectional view of the present laminate in contact with the surface of a metal casting.

A still further application of the present invention is shown in FIG. 5 where a multi-band thermographic laminate 20 is applied to a surface of a metal casting 21 to determine the presence and shape of void spaces 22 which may exist within the casting 21. If the casting 21 is heated slightly, any void spaces 22 will be sharply outlined on the laminate 20 since less heat will pass through the metal casting 21 in the region of the void spaces 22.

The multi-band thermographic laminates may be employed in biomedical applications, e.g., to locate veins or arteries on the skin of an animal, especially an obese animal.

EXAMPLE

The multi-band thermographic laminate of FIG. 2 may be prepared by employing as the liquid crystal compositions:

For Film I:
(by weight) Response Temperature 88°–90° F.
50% oleyl cholesteryl carbonate
50% cholesteryl nonanoate.

For Film II:
(by weight) Response Temperature 86°–88° F.
54% oleyl cholesteryl carbonate
46% cholesteryl nonanoate.

In both films, the liquid crystal compositions are dispersed as discrete aggregates in a polyurethane film as described in U.S. Pat. No. 3,872,050.

Figure 6:
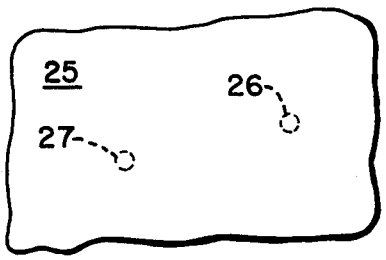
FIG. 6 is a plan view of a skin surface showing schematically two sub-surface tumors which are to be identified by thermographic film methods.
Figure 7:
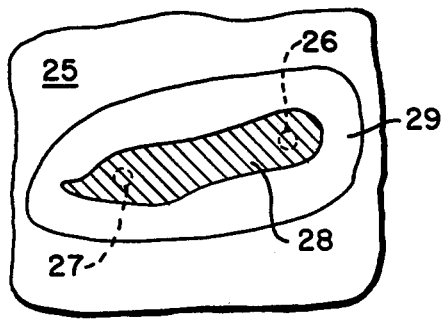
FIG. 7 is a plan view of a single band film thermographic mapping of the skin area of FIG. 6.
Figure 8:
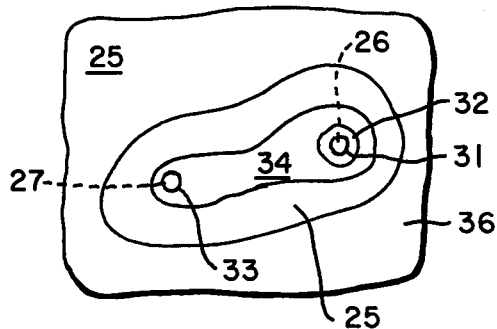
FIG. 8 is a plan view of a multi-band film thermographic mapping of the skin area of FIG. 6.

Multiband thermographic films may be applied to any application where a more detailed temperature profile is needed beyond the one response of a single band thermographic film. For example, in FIG. 6, a hypothetical surface map of a skin surface 25 is presented wherein two subcutaneous tumors 26, 27 are indicated. If this skin surface 25 is mapped with a single band system that begins RED at 33° C., begins GREEN at 34° C. and begins BLUE at 35° C., the resulting temperature contour will be as shown in FIG. 7, i.e., a blue area 28, a green annulus 29 and the remainder 30 of the film red. However if a multiband system of the present invention is employed, having a first response identical with that of the described single band system of FIG. 7 and having an additional band with responses that begin RED at 36° C., begin GREEN at 37° C. and begin BLUE at 38° C., then the multiband system will present the information shown in FIG. 8, wherein a first area 31 is green, an annulus 32 is red; an area 33 is red; a surrounding area 34 is blue; an annular area 35 is green; and the remainder 36 is red. Greater precision in locating the subsurface tumors 26, 27 (heat sources) is achieved.

A further application for multiband systems is in novelty or aesthetic devices where the operator creates a material which is constantly changing colors with changes in the temperature of the environment. For example, in a multiband system, if one band is thermally stabilized made from cholesteryl oleyl carbonate and cholesteryl chloride such that it transforms from iridescent green to transparent isotropic at 20° C., another band is thermally sensitive and begins RED at 23° C., begins GREEN at 31° C. and begins BLUE at 34° C., a multiband system exists such that when worn in contact with the human body (as in a finger ring or as an ornament on a piece of clothing) it is almost always (from -20° C. to 34° C.) displaying an iridescent color and is frequently changing color dynamically as the skin temperature and/or environmental temperature change.

It is also possible to create passive reflectors by utilizing multilayers of thermally stabilized liquid crystals in polyurethane. For example, in the article "Twisted Nematic Display with Cholesteric Reflector," T. J. Scheffer, J. PHYS. D.: Appl. Phys., Vol 8, 1975, there is described a thermally stabilized cholesteric system with a high degree of circularly polarized reflection.

Figure 9:
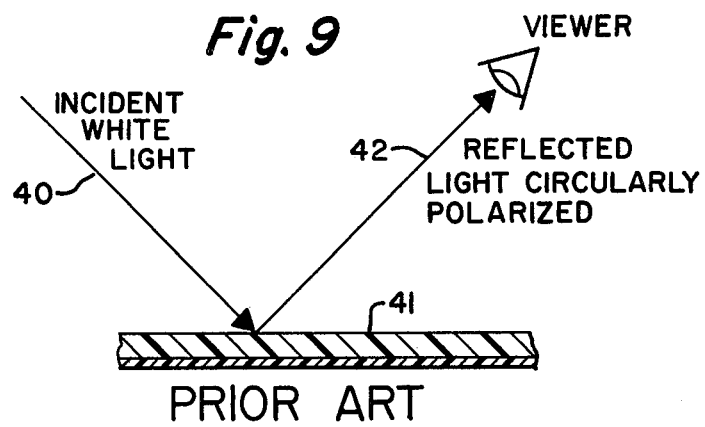
FIG. 9 is a schematic illustration of a white incident light beam and its reflected beam from a single band film of liquid crystal composition.

This is illustrated in FIG. 9 which shows an incident beam 40 of white light reflected from a film 41 of liquid crystal composition—single band. The reflected light beam 42 will be circularly polarized and will have the color corresponding to the response color of the film 41.

Figure 10:
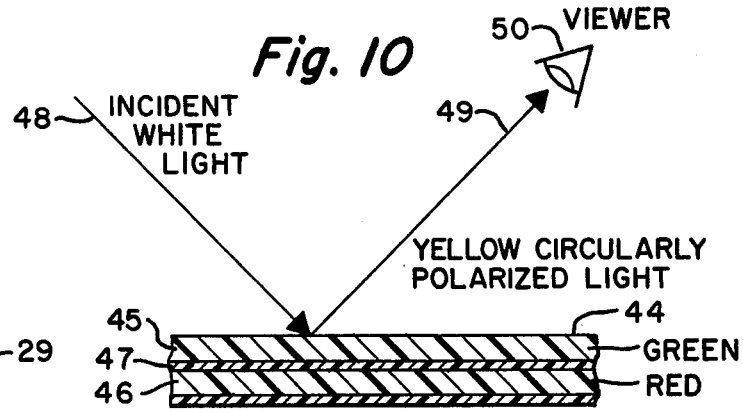
FIG. 10 is a schematic illustration of an incident light beam and its reflected light beam from a two-band film of liquid crystal compositions of this invention.

By employing a multi-band film of two different thermally stabilized liquid crystal compositions, some interesting results are observed., as indicated in FIG. 10 wherein a multi-band film 44 has a green response film 45 and a red response film 46 separated by a clear barrier film 47. An incident beam 48 of white light will be reflected as a beam 49 which has a greater content of circular polarization than the beam 42 of FIG. 9. Moreover the reflected beam 49 will appear yellow to an observer at 50.

Figure 11:
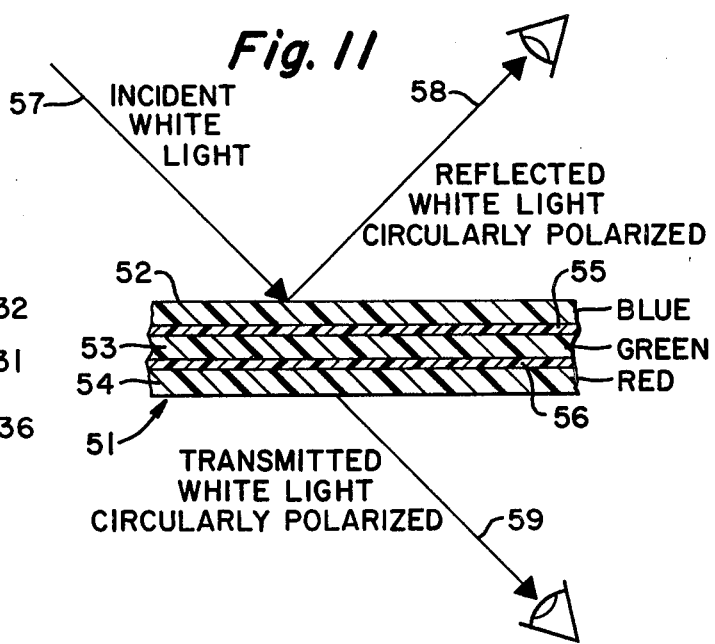
FIG. 11 is a schematic illustration of an incident light beam, its reflected and transmitted light beams from and through a three-band film of this invention.

A still further phenomenon of the present multi-band films is illustrated in FIG. 11 wherein a three-layer film 51 has a thermally stabilized blue response film 52, a green response film 53 and a red response film 54 separated by clear barrier films 55, 56. An incident beam 57 of white light is reflected as a beam 58 of circularly polarized white light. Interestingly the incident beam 57 will be transmitted through the film 51 as a transmitted beam 59 of white light which is circularly polarized in the opposite direction from the polarization of the reflected beam 58. By utilizing a multiband reflector system comprising a green and red thermally stabilized liquid crystal composition, one creates a yellow multiband system reflecting a greater amount of circularly polarized light than would result from a single band system. A multilayer film comprising a red, blue and green layer would comprise a white light reflector, creating reflected circularly polarized white light of one sense (dextro or laevo) and transmitted circularly polarized white light of the opposite sense.

We claim:

1. A multi-band liquid crystal laminate comprising
   (a) a black base film;
   (b) a first polyurethane film containing discrete aggregates of temperature-responsive liquid crystals having a selected response;
   (c) a transparent barrier applied to said first polyurethane film;
   (d) a second polyurethane film containing discrete aggregates of temperature-responsive liquid crystals having a response different from that of said first polyurethane film;
   (e) a transparent barrier applied to said second polyurethane film.

2. The laminate of claim 1 wherein the discrete aggregates of liquid crystals have particle sizes from 0.1 to 20 microns.

3. The laminate of claim 1 wherein the said polyurethane films have a thickness of 5 to 100 microns.

4. A laminate according to claim 1 wherein the said barrier film is polyethylene terephthalate.

5. The laminate of claim 1 wherein all of the said liquid crystals are temperature-responsive and the said laminate contains additional polyurethane films, each separated from the previous film by means of a transparent impervious film and wherein the response temperature of each succeeding film is lower than that of the previously applied film.

6. The laminate of claim 1 wherein each polyurethane film has a liquid crystal content from 5 to 50 weight percent.

7. A multi-band thermographic laminate comprising
   (a) a black base film;
   (b) a first polyurethane film containing discrete aggregates of temperature-responsive liquid crystals having a selected response temperature;
   (c) a transparent barrier applied to said first polyurethane film;
   (d) a second polyurethane film containing discrete aggregates of temperature-responsive liquid crystals having a response temperature lower than that of said first polyurethane film;
   (e) a transparent barrier applied to said second polyurethane film.

8. A multi-band liquid crystal film laminate comprising:
   (a) a base film;
   (b) a first polyurethane film containing discrete aggregates of thermally stabilized liquid crystals having a selected color response;
   (c) a transparent barrier film applied to the said first polyurethane film;
   (d) a second polyurethane film containing discrete aggregates of thermally stabilized liquid crystals having a selected color response differing from that of the said first polyurethane film;
   (e) a transparent barrier applied to the said second polyurethane film.

9. A multi-band liquid crystal film laminate as defined in claim 8 including:
   a third polyurethane film containing discrete aggregates of thermally stabilized liquid crystals having a selected color response differing from that of the said first polyurethane film and also differing from that of the said second polyurethane film; and
   a transparent barrier applied to the said third polyurethane film.

10. A method for generating circularly polarized light which comprises reflecting a beam of light against a multi-band liquid crystal laminate as defined in claim 8 or claim 9.

11. A method for generating circularly polarized light which comprises transmitting a beam of light through a liquid crystal film laminate as defined in claim 8 or claim 9.

12. A method for determining the size, shape and location of void spaces in a metal article which comprises:
   (a) applying a multi-band thermographic film laminate to a surface of the said metal article;
   (b) changing the temperature of the said metal article through a range which includes the response temperature of at least one band of the said multi-band thermographic film laminate;
   (c) generating a visible color response of the said multi-band thermographic film laminate corresponding to the size, shape and location of the said void spaces.

13. A method for determining the size, shape and location of heat sources beneath a surface which comprises:
   (a) applying a multi-band thermographic film laminate to the said surface;
   (b) generating a visible color response of the said multi-band thermographic film laminate corresponding to the size, shape and location of the said heat sources.

* * * * *